US012011365B2

(12) United States Patent
Jimenez et al.

(10) Patent No.: US 12,011,365 B2
(45) Date of Patent: Jun. 18, 2024

(54) TRANSVERSELY EXPANDABLE MINIMALLY INVASIVE INTER VERTEBRAL CAGE

(71) Applicant: Octagon Spine LLC, Seattle, WA (US)

(72) Inventors: Omar F. Jimenez, Seattle, WA (US); Yefim I. Safris, Golden Valley, MN (US)

(73) Assignee: Octagon Spine LLC, Bellevue, WA (US)

(*) Notice: Subject to any disclaimer, the term of this patent is extended or adjusted under 35 U.S.C. 154(b) by 0 days.

(21) Appl. No.: 17/866,896

(22) Filed: Jul. 18, 2022

(65) Prior Publication Data

US 2024/0016622 A1    Jan. 18, 2024

(51) Int. Cl.
*A61F 2/44*  (2006.01)
*A61F 2/30*  (2006.01)

(52) U.S. Cl.
CPC .. *A61F 2/4455* (2013.01); *A61F 2002/30405* (2013.01)

(58) Field of Classification Search
CPC ................ A61F 2/44–447; A61F 2002/30405
See application file for complete search history.

(56) References Cited

U.S. PATENT DOCUMENTS

| 283,218 | A | 8/1883 | Rycke |
| 703,251 | A | 6/1902 | Haire |
| 811,344 | A | 1/1906 | Wands |
| 1,388,836 | A | 8/1921 | Ripsch et al. |
| 1,500,859 | A | 7/1924 | Wright |
| 1,547,946 | A | 7/1925 | Myers |
| 2,106,088 | A | 1/1938 | De Tar |
| 2,231,221 | A | 2/1941 | Rector |
| 2,453,656 | A | 11/1948 | Bullard, III |
| 2,666,334 | A | 1/1954 | Nalle |
| 2,711,105 | A | 6/1955 | Williams |
| 2,842,976 | A | 7/1958 | Young |

(Continued)

FOREIGN PATENT DOCUMENTS

| EP | 1342456 A1 | 9/2003 |
| EP | 1552797 A2 | 7/2005 |

(Continued)

OTHER PUBLICATIONS

PCT/US2010/042941, filed Jul. 22, 2010, International Search Report and Written Opinion, dated Apr. 25, 2011.

(Continued)

*Primary Examiner* — Nicholas J Plionis
(74) *Attorney, Agent, or Firm* — Merchant & Gould P.C.

(57) ABSTRACT

Disclosed herein are systems and methods for intervertebral body fusion that provide more robust support within the disc space. Intervertebral body fusion devices can have a unitary monolithic body including a plurality of body segments interconnected with each other by flexure members. Devices be configured to be inserted through an opening in a compressed configuration and then expanded within the disc space to an expanded configuration. In the expanded configuration, devices can have a greater mediolateral or transverse to the disc space footprint. This wider footprint provides greater support for the vertebrae relative to the size of the opening through which the device is inserted.

17 Claims, 11 Drawing Sheets

(56) References Cited

U.S. PATENT DOCUMENTS

| | | |
|---|---|---|
| 2,891,408 A | 6/1959 | Burt, Jr. |
| 3,386,128 A | 6/1968 | Vyvyan |
| 3,449,971 A | 6/1969 | Posh |
| 3,575,475 A | 4/1971 | Boerner |
| 3,596,863 A | 8/1971 | Kaspareck |
| 3,597,938 A | 8/1971 | Hellen |
| 3,700,289 A | 10/1972 | Bilinski et al. |
| 3,700,290 A | 10/1972 | Ensinger |
| 3,708,925 A | 1/1973 | Ainoura |
| 3,709,132 A | 1/1973 | Farrell et al. |
| 3,916,596 A | 11/1975 | Hawley |
| 3,985,000 A | 10/1976 | Hartz |
| 3,988,906 A | 11/1976 | Smith |
| 4,261,211 A | 4/1981 | Haberland |
| 4,396,047 A | 8/1983 | Balkus |
| 4,478,109 A | 10/1984 | Kobelt |
| 4,516,303 A | 5/1985 | Kloster |
| 4,528,864 A | 7/1985 | Craig |
| 4,559,717 A | 12/1985 | Scire et al. |
| 4,630,495 A | 12/1986 | Smith |
| 4,691,586 A | 9/1987 | van Leijenhorst et al. |
| 4,694,703 A | 9/1987 | Routson |
| 4,869,552 A | 9/1989 | Tolleson et al. |
| 5,133,108 A | 7/1992 | Esnault |
| 5,172,442 A | 12/1992 | Bartley et al. |
| 5,181,371 A | 1/1993 | DeWorth |
| 5,196,857 A | 3/1993 | Chiappetta et al. |
| 5,198,932 A | 3/1993 | Takamura |
| 5,222,986 A | 6/1993 | Wright |
| 5,313,852 A | 5/1994 | Arena |
| 5,374,556 A | 12/1994 | Bennett et al. |
| 5,439,377 A | 8/1995 | Milanovich |
| 5,445,471 A | 8/1995 | Wexler et al. |
| 5,554,191 A | 9/1996 | Lahille et al. |
| 5,645,599 A | 7/1997 | Samani |
| 5,653,763 A | 8/1997 | Errico et al. |
| 5,664,457 A | 9/1997 | Nejati |
| 5,904,479 A | 5/1999 | Staples |
| 5,960,670 A | 10/1999 | Iverson et al. |
| 5,980,252 A | 11/1999 | Samchukov et al. |
| 5,988,006 A | 11/1999 | Fleytman |
| 6,039,761 A | 3/2000 | Li et al. |
| 6,045,579 A | 4/2000 | Hochshuler et al. |
| 6,056,491 A | 5/2000 | Hsu |
| 6,080,193 A | 6/2000 | Hochshuler et al. |
| 6,136,031 A | 10/2000 | Middleton |
| 6,175,989 B1 | 1/2001 | Carpentar et al. |
| 6,315,797 B1 | 11/2001 | Middleton |
| 6,350,317 B1 | 2/2002 | Hao et al. |
| 6,378,172 B1 | 4/2002 | Schrage |
| 6,395,035 B2 | 5/2002 | Bresina et al. |
| 6,454,806 B1 | 9/2002 | Cohen et al. |
| 6,454,807 B1 | 9/2002 | Jackson |
| 6,484,608 B1 | 11/2002 | Ziavras |
| 6,517,772 B1 | 2/2003 | Woolf |
| 6,554,526 B1 | 4/2003 | Egelandsdal |
| 6,616,695 B1 | 9/2003 | Crozet et al. |
| 6,641,614 B1 | 11/2003 | Wagner et al. |
| 6,719,796 B2 | 4/2004 | Cohen et al. |
| 6,752,832 B2 | 6/2004 | Neumann |
| 6,772,479 B2 | 8/2004 | Hinkley et al. |
| 6,802,229 B1 | 10/2004 | Lambert |
| 6,808,537 B2 | 10/2004 | Michelson |
| 6,863,673 B2 | 3/2005 | Gerbec et al. |
| 6,932,844 B2 | 8/2005 | Ralph et al. |
| 6,953,477 B2 | 10/2005 | Berry |
| 7,018,415 B1 | 3/2006 | McKay |
| 7,051,610 B2 | 5/2006 | Stoianovici et al. |
| 7,070,598 B2 | 7/2006 | Lim et al. |
| 7,087,055 B2 | 8/2006 | Lim et al. |
| 7,201,751 B2 | 4/2007 | Zucherman et al. |
| 7,273,373 B2 | 9/2007 | Horiuchi |
| 7,308,747 B2 | 12/2007 | Smith et al. |
| 7,316,381 B2 | 1/2008 | Häcker et al. |
| 7,410,201 B1 | 8/2008 | Wilson et al. |
| 7,425,103 B2 | 9/2008 | Perez-Sanchez |
| 7,431,735 B2 | 10/2008 | Liu et al. |
| 7,435,032 B1 | 10/2008 | Murphey et al. |
| 7,547,325 B2 | 6/2009 | Biedermann et al. |
| 7,584,682 B2 | 9/2009 | Hsiao |
| 7,611,538 B2 | 11/2009 | Belliard et al. |
| 7,632,281 B2 | 12/2009 | Errico et al. |
| 7,674,296 B2 | 3/2010 | Rhoda et al. |
| 7,682,376 B2 | 3/2010 | Trieu |
| 7,708,779 B2 | 5/2010 | Edie et al. |
| 7,712,389 B2 | 5/2010 | Wang |
| 7,753,958 B2 | 7/2010 | Gordon et al. |
| 7,758,645 B2 | 7/2010 | Studer |
| 7,758,648 B2 | 7/2010 | Castleman et al. |
| 7,892,285 B2 | 2/2011 | Viker |
| 7,896,919 B2 | 3/2011 | Belliard et al. |
| 7,901,409 B2 | 3/2011 | Canaveral et al. |
| 7,947,078 B2 | 5/2011 | Siegal |
| 7,951,199 B2 | 5/2011 | Miller |
| 7,985,256 B2 | 7/2011 | Grotz et al. |
| 8,057,549 B2 | 11/2011 | Butterman et al. |
| 8,070,813 B2 | 12/2011 | Grotz et al. |
| 8,088,163 B1 | 1/2012 | Kleiner |
| 8,192,495 B2 | 6/2012 | Simpson et al. |
| 8,303,663 B2 | 11/2012 | Jimenez et al. |
| 8,496,706 B2 | 7/2013 | Ragab et al. |
| 8,523,944 B2 | 9/2013 | Jimenez et al. |
| 8,540,452 B2 | 9/2013 | Jimenez et al. |
| 8,628,577 B1 | 1/2014 | Jimenez |
| 8,636,746 B2 | 1/2014 | Jimenez et al. |
| 8,771,360 B2 | 7/2014 | Jimenez et al. |
| 8,795,366 B2 | 8/2014 | Varela |
| 8,894,712 B2 | 11/2014 | Varela |
| 8,906,100 B2 | 12/2014 | Jimenez |
| 8,932,302 B2 | 1/2015 | Jimenez et al. |
| 8,940,049 B1 | 1/2015 | Jimenez et al. |
| 9,358,125 B2 | 6/2016 | Jimenez et al. |
| 9,381,092 B2 | 7/2016 | Jimenez et al. |
| 9,445,917 B2 | 9/2016 | Jimenez et al. |
| 9,474,626 B2 | 10/2016 | Jimenez |
| 9,486,328 B2 | 11/2016 | Jimenez |
| 9,498,270 B2 | 11/2016 | Jimenez |
| 9,668,879 B2 | 6/2017 | Jimenez et al. |
| 9,867,717 B2 | 1/2018 | Jimenez |
| 10,060,469 B2 | 8/2018 | Jimenez et al. |
| 2002/0128716 A1 | 9/2002 | Cohen et al. |
| 2002/0138146 A1 | 9/2002 | Jackson |
| 2003/0077110 A1 | 4/2003 | Knowles |
| 2003/0023314 A1 | 12/2003 | Landry et al. |
| 2004/0049271 A1 | 3/2004 | Biedermann et al. |
| 2004/0111157 A1 | 6/2004 | Ralph et al. |
| 2004/0153156 A1 | 8/2004 | Coben et al. |
| 2004/0193158 A1 | 9/2004 | Lim |
| 2004/0225364 A1 | 11/2004 | Richelsoph et al. |
| 2005/0000228 A1 | 1/2005 | De Sousa et al. |
| 2005/0033431 A1 | 2/2005 | Gordon et al. |
| 2005/0095384 A1 | 5/2005 | Wittmeyer, Jr. |
| 2005/0113921 A1 | 5/2005 | An et al. |
| 2005/0113924 A1 | 5/2005 | Buttermann |
| 2005/0175406 A1 | 8/2005 | Perez-Sanchez |
| 2005/0182416 A1 | 8/2005 | Lim et al. |
| 2005/0261769 A1 | 11/2005 | Moskowitz et al. |
| 2006/0004447 A1 | 1/2006 | Mastrorio et al. |
| 2006/0004455 A1 | 1/2006 | Leonard et al. |
| 2006/0025862 A1 | 2/2006 | Villiers et al. |
| 2006/0058878 A1 | 3/2006 | Michelson |
| 2006/0129244 A1 | 6/2006 | Ensign |
| 2006/0149385 A1 | 7/2006 | McKay |
| 2006/0184171 A1 | 8/2006 | Biedermann et al. |
| 2006/0247781 A1 | 11/2006 | Francis |
| 2006/0253201 A1 | 11/2006 | McLuen |
| 2006/0293752 A1 | 12/2006 | Mounmene et al. |
| 2007/0032791 A1 | 2/2007 | Greenhalgh et al. |
| 2007/0049943 A1 | 3/2007 | Moskowitz et al. |
| 2007/0083267 A1 | 4/2007 | Miz et al. |
| 2007/0093901 A1 | 4/2007 | Grotz et al. |
| 2007/0129730 A1 | 6/2007 | Woods et al. |
| 2007/0173826 A1 | 7/2007 | Canaveral |
| 2007/0185577 A1 | 8/2007 | Malek |

(56) References Cited

U.S. PATENT DOCUMENTS

| | | |
|---|---|---|
| 2007/0191954 A1 | 8/2007 | Hansell et al. |
| 2007/0191958 A1 | 8/2007 | Abdou |
| 2007/0198089 A1 | 8/2007 | Moskowitz et al. |
| 2007/0219634 A1 | 9/2007 | Greenhalgh et al. |
| 2007/0222100 A1 | 9/2007 | Husted et al. |
| 2007/0250171 A1 | 10/2007 | Bonin, Jr. |
| 2007/0255415 A1 | 11/2007 | Edie et al. |
| 2007/0282449 A1 | 12/2007 | de Villiers et al. |
| 2007/0288092 A1 | 12/2007 | Bambakidis |
| 2007/0293329 A1 | 12/2007 | Glimpel et al. |
| 2007/0293948 A1 | 12/2007 | Bagga et al. |
| 2008/0026903 A1 | 1/2008 | Flugrad et al. |
| 2008/0077246 A1 | 3/2008 | Fehling et al. |
| 2008/0091211 A1 | 4/2008 | Gately |
| 2008/0100179 A1 | 5/2008 | Ruggeri et al. |
| 2008/0103601 A1 | 5/2008 | Biro et al. |
| 2008/0114367 A1 | 5/2008 | Meyer |
| 2008/0140207 A1 | 6/2008 | Olmos |
| 2008/0147194 A1 | 6/2008 | Grotz et al. |
| 2008/0154266 A1 | 6/2008 | Protopsaltis et al. |
| 2008/0161920 A1 | 7/2008 | Melkent |
| 2008/0161931 A1 | 7/2008 | Perez-Cruet et al. |
| 2008/0168855 A1 | 7/2008 | Giefer et al. |
| 2008/0183204 A1 | 7/2008 | Greenhalgh et al. |
| 2008/0188941 A1 | 8/2008 | Grotz |
| 2008/0210039 A1 | 9/2008 | Brun |
| 2008/0221694 A1 | 9/2008 | Warnick et al. |
| 2008/0234736 A1 | 9/2008 | Trieu et al. |
| 2008/0243255 A1* | 10/2008 | Butler .................. A61F 2/4465 623/17.11 |
| 2008/0281423 A1 | 11/2008 | Sheffer et al. |
| 2008/0292392 A1 | 11/2008 | Voellmer |
| 2008/0319487 A1 | 12/2008 | Fielding et al. |
| 2009/0012564 A1 | 1/2009 | Chirico et al. |
| 2009/0076614 A1 | 3/2009 | Arramon |
| 2009/0099568 A1 | 4/2009 | Lowry et al. |
| 2009/0164017 A1 | 6/2009 | Sommerich et al. |
| 2009/0210061 A1 | 8/2009 | Sledge |
| 2009/0222100 A1 | 9/2009 | Cipoletti et al. |
| 2009/0234362 A1 | 9/2009 | Blain et al. |
| 2009/0259316 A1 | 10/2009 | Ginn et al. |
| 2009/0299478 A1 | 12/2009 | Carls et al. |
| 2009/0306672 A1 | 12/2009 | Reindel et al. |
| 2010/0004688 A1 | 1/2010 | Maas et al. |
| 2010/0076557 A1 | 3/2010 | Miller |
| 2010/0082109 A1 | 4/2010 | Greenhalgh et al. |
| 2010/0094305 A1 | 4/2010 | Chang et al. |
| 2010/0161062 A1 | 6/2010 | Foley et al. |
| 2010/0185291 A1 | 7/2010 | Jimenez et al. |
| 2010/0192715 A1 | 8/2010 | Vauchel et al. |
| 2010/0209184 A1 | 8/2010 | Jimenez et al. |
| 2011/0015638 A1 | 1/2011 | Pischl et al. |
| 2011/0054616 A1 | 3/2011 | Kamran et al. |
| 2011/0093075 A1 | 4/2011 | Duplessis et al. |
| 2011/0112644 A1 | 5/2011 | Zilberstein et al. |
| 2011/0138948 A1 | 6/2011 | Jimenez et al. |
| 2011/0160861 A1 | 6/2011 | Jimenez et al. |
| 2011/0172774 A1 | 7/2011 | Varela |
| 2011/0270398 A1 | 11/2011 | Grotz et al. |
| 2012/0010653 A1 | 1/2012 | Seifert et al. |
| 2012/0029636 A1 | 2/2012 | Ragab et al. |
| 2012/0083887 A1 | 4/2012 | Purcell et al. |
| 2012/0116518 A1 | 5/2012 | Grotz et al. |
| 2012/0158071 A1 | 6/2012 | Jimenez et al. |
| 2012/0185049 A1 | 7/2012 | Varela |
| 2012/0226357 A1 | 9/2012 | Varela |
| 2012/0271419 A1 | 10/2012 | Marik |
| 2012/0290094 A1 | 11/2012 | Lim et al. |
| 2012/0303124 A1 | 11/2012 | McLuen et al. |
| 2012/0323329 A1 | 12/2012 | Jimenez et al. |
| 2013/0053966 A1 | 2/2013 | Jimenez et al. |
| 2013/0144388 A1 | 6/2013 | Emery et al. |
| 2013/0158664 A1 | 6/2013 | Palmatier et al. |
| 2013/0197642 A1 | 8/2013 | Ernst |
| 2013/0317615 A1 | 11/2013 | Jimenez et al. |
| 2014/0012383 A1 | 1/2014 | Triplett et al. |
| 2014/0018924 A1 | 1/2014 | McManus et al. |
| 2014/0039622 A1 | 2/2014 | Glerum et al. |
| 2014/0058512 A1 | 2/2014 | Petersheim |
| 2014/0088714 A1 | 3/2014 | Miller et al. |
| 2014/0140757 A1 | 5/2014 | Jimenez et al. |
| 2014/0156007 A1 | 6/2014 | Pabst et al. |
| 2014/0194991 A1 | 7/2014 | Jimenez |
| 2014/0236296 A1 | 8/2014 | Wagner et al. |
| 2014/0249629 A1 | 9/2014 | Moskowitz et al. |
| 2014/0277490 A1 | 9/2014 | Perloff et al. |
| 2014/0343608 A1 | 11/2014 | Whiton et al. |
| 2015/0018951 A1 | 1/2015 | Leobl |
| 2015/0088258 A1 | 3/2015 | Jimenez et al. |
| 2015/0100128 A1 | 4/2015 | Glerum et al. |
| 2015/0148908 A1 | 5/2015 | Marino et al. |
| 2015/0230929 A1 | 8/2015 | Lorio |
| 2015/0272743 A1 | 10/2015 | Jimenez et al. |
| 2015/0272745 A1 | 10/2015 | Jimenez et al. |
| 2015/0272746 A1 | 10/2015 | Jimenez et al. |
| 2015/0351925 A1 | 12/2015 | Emerick et al. |
| 2016/0262907 A1 | 9/2016 | Jimenez |
| 2016/0356368 A1 | 12/2016 | Jimenez et al. |
| 2017/0056179 A1* | 3/2017 | Lorio ................. B23K 15/0093 |
| 2017/0056200 A1 | 3/2017 | Koch et al. |
| 2020/0281743 A1* | 9/2020 | Jimenez .................. A61F 2/447 |

FOREIGN PATENT DOCUMENTS

| | | | |
|---|---|---|---|
| EP | 1881209 A1 | 1/2008 | |
| JP | 05-81194 | 4/1993 | |
| JP | 2004-301135 A | 10/2004 | |
| JP | 2008-208932 A | 9/2008 | |
| WO | WO 2004/026188 A2 | 4/2004 | |
| WO | WO 2004/109155 A1 | 12/2004 | |
| WO | WO 2005/081330 A2 | 9/2005 | |
| WO | WO 2005/096975 A2 | 10/2005 | |
| WO | WO 2006/094535 A1 | 9/2006 | |
| WO | WO 2006/116052 A2 | 11/2006 | |
| WO | WO 2006/125329 A1 | 11/2006 | |
| WO | WO 2007/002583 A2 | 1/2007 | |
| WO | WO 2007/009107 A2 | 1/2007 | |
| WO | WO 2007/028140 A2 | 3/2007 | |
| WO | WO 2007/076377 A2 | 7/2007 | |
| WO | WO 2007/111979 A2 | 10/2007 | |
| WO | WO 2008/137192 A1 | 11/2008 | |
| WO | WO 2009/018349 A2 | 2/2009 | |
| WO | WO 2010/078468 A2 | 7/2010 | |
| WO | WO 2010/078520 A2 | 7/2010 | |
| WO | WO 2011/011609 A2 | 1/2011 | |
| WO | WO 2011/011626 A2 | 1/2011 | |
| WO | WO 2014/066890 A1 | 5/2014 | |

OTHER PUBLICATIONS

PCT/US2010/042915, filed Jul. 22, 2010, Search Report and Written Opinion dated Apr. 22, 2011.
PCT/US2009/069876, filed Dec. 30, 2009, International Search Report and Written Opinion dated Sep. 27, 2010, 10 pages.
PCT/US2009/069958, filed Dec. 31, 2009, International Search Report and Written Opinion dated Nov. 29, 2010, 7 pages.
PCT/US2015/055449, filed Oct. 14, 2015, International Search Report and Written Opinion dated Dec. 11, 2015, 9 pages.
PCT/US2015/032977, filed May 28, 2015, International Search Report and Written Opinion dated Sep. 21, 2015, 10 pages.
European Application No. EP 09837185.9, European Search Report dated May 14, 2013, 7 pages.
Japanese Application No. 2012-521784, JP Office Action dated Feb. 18, 2014, 8 pages.
PCT/US2013/067070, PCT Written Opinion/Search Report dated Feb. 27, 2014, 14 pages.
PCT/US2014/052913, PCT Written Opinion/Search Report dated Dec. 22, 2014, 10 pages.
European Application No. EP 10802916.6, Examination Report dated May 12, 2016, 4 pages.
Canadian Application No. 2,768,867, Office Action dated Aug. 4, 2016, 4 pages.

(56) References Cited

OTHER PUBLICATIONS

Canadian Application No. 2,768,867, Office Action dated Apr. 19, 2017, 4 pages.
European Application No. EP14887838.2, Extended European Search Report, dated Oct. 25, 2017, 8 pages.
Wenzel Spine, Inc., VariLift®-L Expandable Interbody Fusion Device: A proven solution for stand-alone fusion, Product Overview, 12 pages, 2010.
Peter A Halverson, et. al., Tension-based Multi-stable Compliant: Rolling-contact Elements, Department of Mechanical Engineering, Brigham Young University, Provo UT, USA 84602, 34 pages, 2007.
Just L. Herder, Force Directed Design of Laparoscopic Forceps, ASME Design Engineering Technical Conference, 8 pages, 1998.
Alexander H. Slocum, Fundamentals of Design, 2005.
W. Küsswetter, A Supplementary Instrumentation for Posterior Fusion of Spine in Scoliosis, Archives of Orthopedic Traumatic Surgery, 1980, 1 page.
Chou et al., Efficacy of Anterior Cervical Fusion: Comparison of Titanium Cages, polyetheretherketone (PEEK) cages and autogenous bone grafts, Journal of Clinical Neuroscience, 2008, pp. 1240-1245.
Amelie Jeanneau, et. al., A Compliant Rolling Contact Joint and its Application in a 3-DOF Planar Parallel Mechanism with Kinematic Analysis, ASME, Design Engineering Technical Conferences, 9 pages, 2004.
Hunter et al., Overview of Medical Devices, Department of Radiology, University of Arizona, Aug. 2001, pp. 89-140, vol. 30, No. 4, ISSN: 0363-0188.
Medtronic Sofamor Danek USA, Inc., Capstone Instrument Set Technique, http://www.mtortho.com/public/capstone.pdf, © 2005, 25 pages.
Medtronic, Capstone Peek Spinal System Surgical Technique, http://www.mtortho.com/public/capstone_peek_st.pdf, © 2009, 36 pages.
Website printout from https://seelio.com/w/fgf/omnilif-the-new-standard-in-spinal-deformity-correction-and-fusion?student=lumbarjax; dated Nov. 27, 2014, 5 pages.
Printout from Video for OmniLIF Anterior Insertion Approach from Lumber Jax; https://seelio.com/w/fgf/omnilif-the-new-standard-in-spinal-deformity-correction-and-fusion?student=lumbarjax; dated Nov. 27, 2014, 7 pages.
Printout from Video for OmniLIF Features from Lumber Jax; https://seelio.com/w/fgf/omnilif-the-new-standard-in-spinal-deformity-correction-and-fusion?student=lumbarjax; dated Nov. 27, 2014, 11 pages.
International Search Report and Written Opinipn for International Application No. PCT/US2019/068890 dated Apr. 29, 2020.
International Search Report and Written Opinion for International Application No. PCT/US2023/028048 dated Aug. 21, 2021.
Australian Examination Report for Application No. 2019433217 dated Oct. 31, 2022, 3 pages.

\* cited by examiner

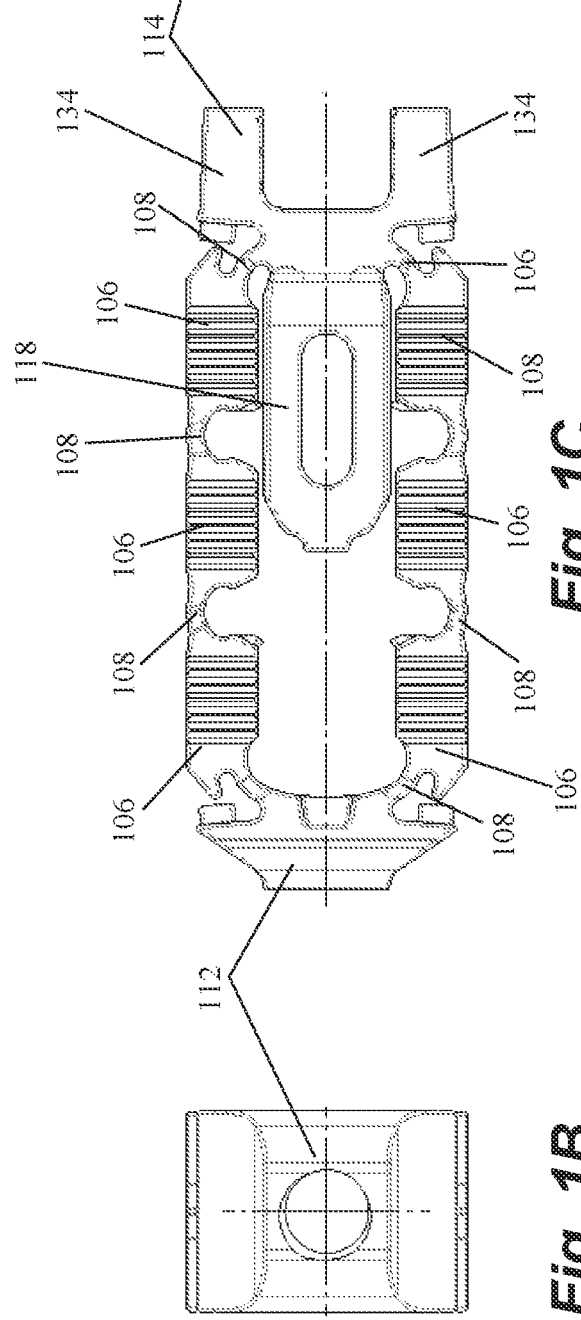
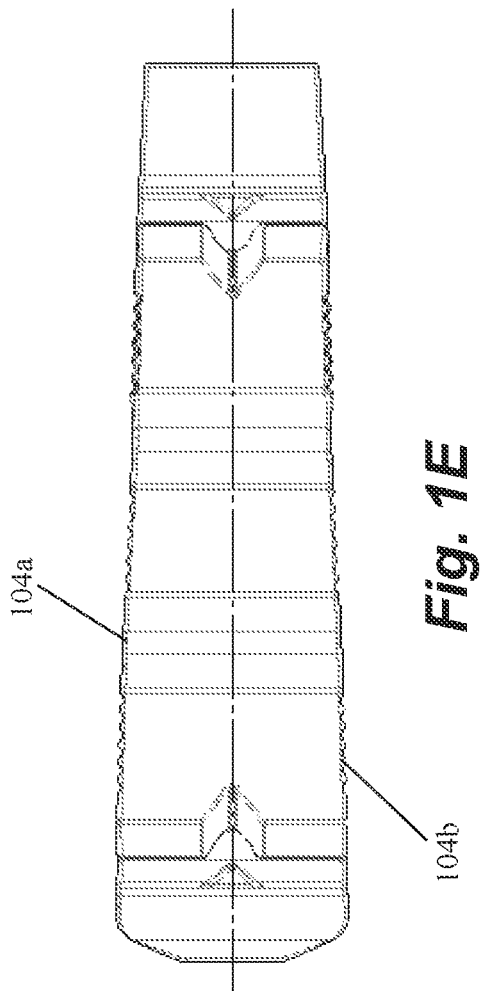

TRANSVERSELY EXPANDABLE MINIMALLY INVASIVE INTER VERTEBRAL CAGE

TECHNICAL FIELD

The present disclosure relates to the fusion of vertebral bodies. More specifically, the present disclosure relates to devices and associated methods for fusion of vertebral bodies that provide robust spinal support in a less invasive manner.

BACKGROUND

The concept of intervertebral fusion for the cervical and lumbar spine following a discectomy was generally introduced in the 1960s. It involved coring out a bone graft from the hip and implanting the graft into the disc space. The disc space was prepared by coring out the space to match the implant. The advantages of this concept were that it provided a large surface area of bone to bone contact and placed the graft under loading forces that allowed osteoconduction and induction enhancing bone fusion. However, the technique is seldom practiced today due to numerous disadvantages including lengthy operation time, destruction of a large portion of the disc space, high risk of nerve injury, and hip pain after harvesting the bone graft.

Presently, at least two devices are commonly used to perform the intervertebral portion of an intervertebral body fusion: the first is the distraction device and the second is the intervertebral body fusion device, often referred to as a cage. Cages can be implanted as standalone devices or as part of a circumferential fusion approach with pedicle screws and rods. The concept is to introduce a distraction device that will distract a collapsed disc in a generally axial direction, decompress the nerve root, and allow load sharing to enhance bone formation, and then implant an intervertebral fusion device that is small enough to allow implantation with minimal retraction and pulling on nerves.

In a typical intervertebral body fusion procedure, a portion of the intervertebral disc is first removed from between the vertebral bodies. This can be done through either a direct open approach or a minimally invasive approach. Disc shavers, pituitary rongeours, curettes, and/or disc scrapers can be used to remove the nucleus and a portion of either the anterior or posterior annulus to allow implantation and access to the inner disc space. The distraction device is inserted into the cleared space to enlarge the disc space such that the vertebral bodies are separated in a generally axial direction by actuating the distraction device. Enlarging the disc space is important because it also opens the foramen where the nerve root exists. It is important that during the distraction process one does not over-distract the facet joints. An intervertebral fusion device is next inserted into the distracted space and bone growth factor, such as autograft, a collagen sponge with bone morphogenetic protein, or other bone enhancing substance may be inserted into the space within the intervertebral fusion device to promote the fusion of the vertebral bodies.

Intervertebral distraction and fusion can be performed through anterior, posterior, oblique, and lateral approaches. Each approach has its own anatomical challenges, but the general concept is to fuse adjacent vertebra in the cervical thoracic or lumbar spine. Devices have been made from various materials. Such materials include cadaveric cancellous bone, carbon fiber, titanium and polyetheretherketone (PEEK). Devices have also been made into different shapes such as a bean shape, football shape, banana shape, wedge shape and a threaded cylindrical cage.

As with all minimally invasive surgeries, a primary goal is to provide equivalent or near equivalent treatment as more invasive surgical techniques but with less discomfort, recovery time, etc. for the patient. One problem with minimally invasive intervertebral fusion procedures is that the limited size of the surgical access limits the size of the implant(s) that can be inserted. While devices that are vertically expandable in a generally axial direction have addressed some of these issues by being able to be inserted through a smaller opening and then made taller in a generally axial direction within the disc space, such devices are still limited in the transverse footprint that can be covered within the disc space which can affect the stability of the device within the disc space and limits the area for bone grown. Examples of such devices are disclosed in U.S. Pat. No. 11,234,835 and U.S. Patent Publication No. 2020/0281743, each of which is incorporated herein by reference in its entirety.

SUMMARY

Disclosed herein are systems and methods for intervertebral body fusion that provide more robust support within the disc space. Intervertebral body fusion devices can have a unitary monolithic body including a plurality of body segments interconnected with each other by flexure members. Devices be configured to be inserted through an opening in a compressed configuration and then expanded within the disc space to an expanded configuration. In the expanded configuration, devices can have a greater mediolateral or transverse to the disc space footprint. This wider footprint provides greater support for the vertebrae relative to the size of the opening through which the device is inserted.

In one embodiment, an expandable intervertebral body fusion device includes a unitary monolithic body having a plurality of body segments connected to each other with flexure members and an opening defined between the plurality of body segments. The device body can include an anterior body segment, a posterior body segment and one or more mediolateral body segments extending between the anterior body segment and the posterior body segment along both a lateral side and a medial side of the anterior body segment and the posterior body segment. An opening can be formed in each of the anterior body segment and the posterior body segment. A locking bushing can extend from one of the anterior body segment and the posterior body segment into the opening in the body. The body is configured to be mediolaterally expanded from a compressed configuration to an expanded configuration by interaction of an expansion tool with the threaded opening causing the one or more mediolateral body segments on the lateral side and the one or more mediolateral body segments on the medial side to generally move away from each other and expand the opening between the plurality of body segments such that the body forms a greater mediolateral footprint in the expanded configuration than in the compressed configuration. Further expansion of the body can be prevented by interaction of the locking bushing with the other of the anterior body segment and the posterior body segment.

In one embodiment, an expandable intervertebral body fusion device includes a unitary monolithic body having a plurality of body segments connected to each other with flexure members and an opening defined between the plurality of body segments. The device body can include an anterior body segment, a posterior body segment and one or more mediolateral body segments extending between the anterior body segment and the posterior body segment along both a lateral side and a medial side of the anterior body segment and the posterior body segment. An opening can be formed in each of the anterior body segment and the posterior body segment. The body is configured to be mediolaterally expanded from a compressed configuration to an expanded configuration by interaction of an expansion tool with the threaded opening causing the one or more mediolateral body segments on the lateral side and the one or more mediolateral body segments on the medial side to generally move away from each other and expand the opening between the plurality of body segments such that the body forms a greater mediolateral footprint in the expanded configuration than in the compressed configuration. The mediolateral body segments can include adjacent projections and grooves that form tongue and groove connections between adjacent mediolateral body segments when the body is in the expanded configuration, the tongue and groove connections providing increased resistance of the body to shear and torsional forces.

The above summary is not intended to describe each illustrated embodiment or every implementation of the subject matter hereof. The figures and the detailed description that follow more particularly exemplify various embodiments.

BRIEF DESCRIPTION OF THE DRAWINGS

Subject matter hereof may be more completely understood in consideration of the following detailed description of various embodiments in connection with the accompanying figures, in which:

FIGS. 1A-1F depict an expandable intervertebral body fusion device in a collapsed configuration according to an embodiment.

Figure 1A:
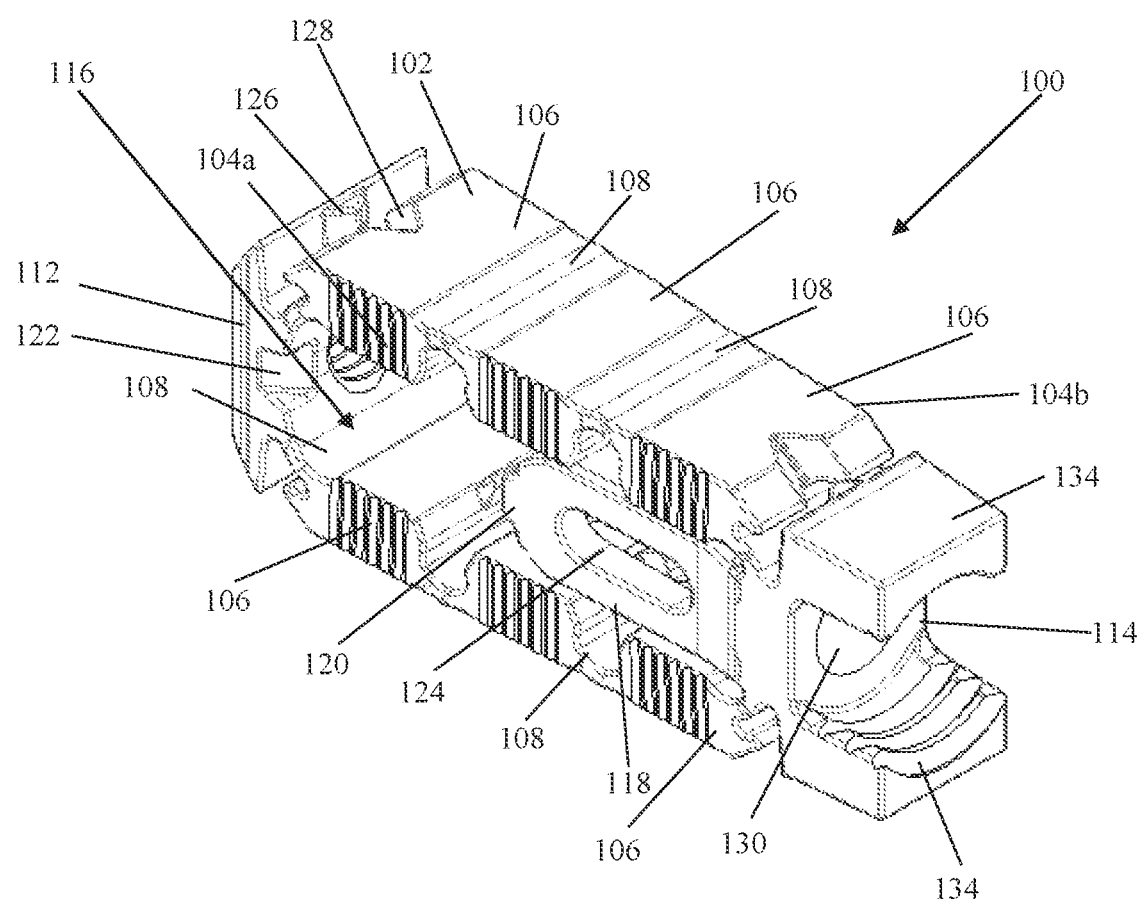

While various embodiments are amenable to various modifications and alternative forms, specifics thereof have been shown by way of example in the drawings and will be described in detail. It should be understood, however, that the intention is not to limit the claimed inventions to the particular embodiments described. On the contrary, the intention is to cover all modifications, equivalents, and alternatives falling within the spirit and scope of the subject matter as defined by the claims.

DETAILED DESCRIPTION OF THE DRAWINGS

FIGS. 1A-1F and 2A-2E depict an expandable intervertebral body fusion device 100 according to an embodiment. FIGS. 1A-1F depict the device 100 in a collapsed configuration and FIGS. 2A-2E depict the device 100 in an expanded configuration. In practice, the device 100 is inserted into the disc space through a minimally invasive access in the collapsed configuration and then expanded inside of the disc space. In embodiments, the device 100 is inserted between adjacent vertebrae 10 on its side (i.e., as shown in FIG. 1E) such that when it is expanded in the disc space rather than expanding vertically it expands horizontally/transversely to the disc space to enable the device to take up a larger footprint within the disc space once the device is expanded. The device is therefore able to occupy more lateral to medial and anterior to posterior space within the disc space relative to the size of the access. In one embodiment in its insertion and un-expanded state the device is 8 mm in height, 11 mm in width and 26 mm in length. The device can have many heights from 8 mm up to 16 mm. In embodiments, the width can go from 8-29 mm and the length from 22 mm-42 mm. When the device is expanded, the height remains the same but the width can double or nearly double (from 11.5 to 22 mm or 47%) and the length goes from 26 mm to 20 mm (16% decrease). The device can have many lordotic angles from 0 to 15 degrees or higher; the most common being 0, 6, 12 degrees. The top and bottom of the device can have different shapes to better fit the endplates such as football shaped or domed. Also, the different segments of the device separated by flexures could be tailored or cut by wire EDM or 3D printed to create different horizontal expanded states such as oval, elliptical, circular, bean shaped, banana shaped or many other polygons and non-polygon shapes. The mean disc height at the L3-4 level is 11.3 mm+/−1.8 mm, L4-5 11.3+/−2.1 mm and L5-S1 10.7+/−2.1 mm. The average circumference of the L4 endplate is about 141 mm and surface area 1,492 mm$^2$ above. The device can have different footprints to try to fill the endplate or disc space circumference. In other embodiments, the device can be expanded vertically to enlarge the disc space.

Referring now to FIGS. 1A-1F, device 100 can include a device body 102. Generally, device body 102 can be unitarily formed as a single monolithic construct, although multiple component embodiments are also contemplated. Device body 102 can include upper 104a and lower 104b bearing surfaces. As noted above, device 100 can be inserted generally on its side such that bearing surfaces 104a, 104b interface with and bear the forces of the adjacent vertebrae. Device body 102 can include a plurality of side body segments 106 unitary connected to each other by flexure 108 comprising a thin, flexible strip of material. Device body 102 can further include a first end body segment 112 and a second end body segment 114 that can also be connected with mediolateral body segments by flexures 108. Side and end body segments and flexures 108 can perform a continuous, unitary outer perimeter surface. In some embodiments, device body 102 is configured to be inserted with first end body segment 112 distal of the surgeon, such that first end body segment 112 is an anterior body segment, second end body segment 114 is a posterior body segment, and side body segments 106 are mediolateral body segments. An interior 116 is defined between the body segments.

In the depicted embodiment, the device 100 includes three mediolateral body segments 106 on each side such that the device includes a total of eight body segments. In some embodiments, a device having eight body segments may be generally octagonally shaped in the expanded configuration as depicted in FIGS. 2A-2E. In other embodiments, device may have greater or fewer mediolateral body segments on each side.

Figure 3A:
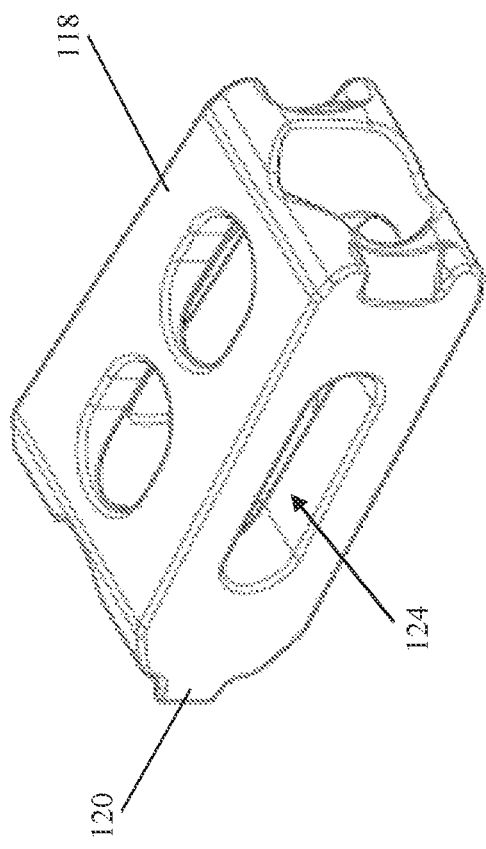
FIGS. 3A-3C depict a portion of an expandable intervertebral body fusion device according to an embodiment.
Figure 3C:
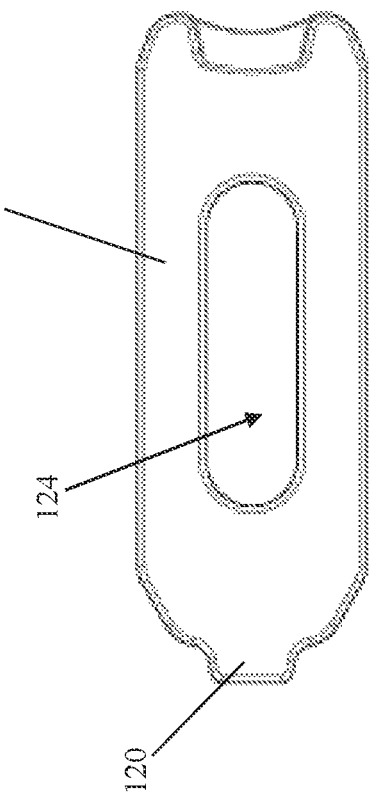
Figure 3B:
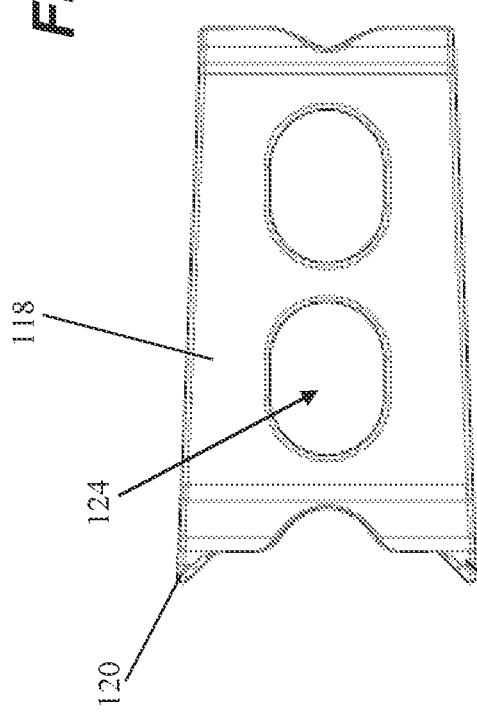

Device body 102 can further include an internal locking bushing 118 that is depicted in isolation in FIGS. 3A-3C that can be unitarily formed with second end body segment 112 and extend axially through the open interior 116 of device body. Locking bushing 118 can have a locking element which, in the depicted embodiment, takes the form of a pair of locking projections 120 on opposing sides of the distal end of locking bushing. When the device 100 is expanded, the locking projections 120 interlock with a corresponding locking element such as a pair of opposing lock apertures 122 disposed on opposing sides of the proximal end of the first end body segment. Once the device is expanded, these locking elements prevent further expansion once the projections 120 nest in the corresponding apertures 122, which prevents damage to the device body 102 that may otherwise result from over-expansion. Locking elements further lock the device in the expanded configuration such that natural forces on device body 102 within the patient's body will not cause the device body 102 to collapse. Locking bushing 118 can include an open interior 124 that can accommodate bone growth material and one or more openings along one or more sides of the device in communication with the open interior. In some embodiments, multiple devices can be provided with locking bushings 118 of different lengths. Devices having locking bushings 118 of various axial lengths provide a surgeon with the flexibility to select a device with a desired degree of expansion for the needs of a given patient. For example, the disc space may not be large enough to accommodate a fully expanded device, so a device having a longer locking bushing can be selected to limit expansion to a predetermined amount that best fits the disc space. In other embodiments, locking bushings 118 are not unitarily formed with device body such that a surgeon can select a locking bushing from a plurality of different locking bushings having different axial lengths, which is then functionally linked to device body with an expansion screw (described in more detail below).

Figure 1F:
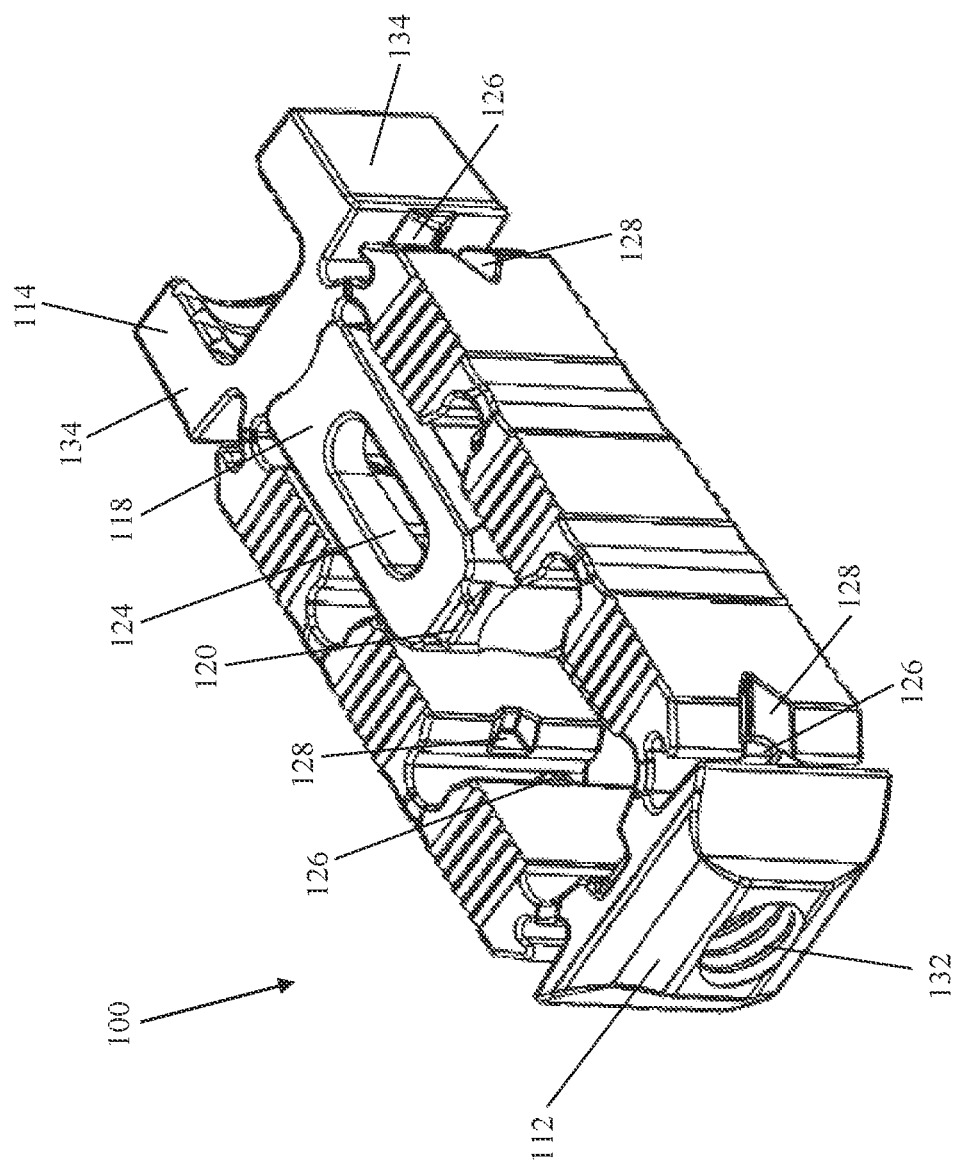
Figures 2A, 2B:
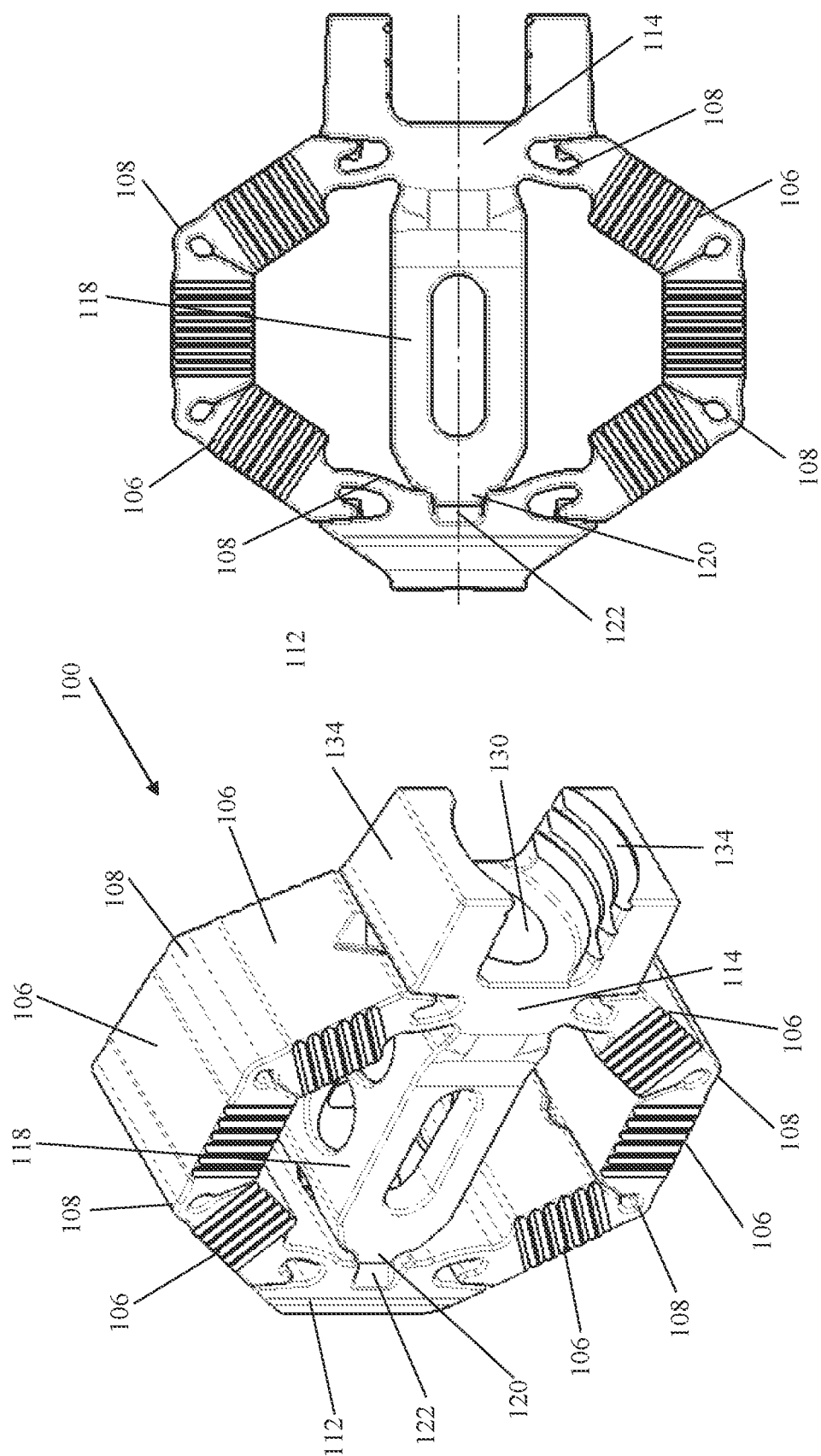
FIGS. 2A-2E depict the expandable intervertebral body fusion device of FIGS. 1A-1F in an expanded configuration.
Figure 2E:
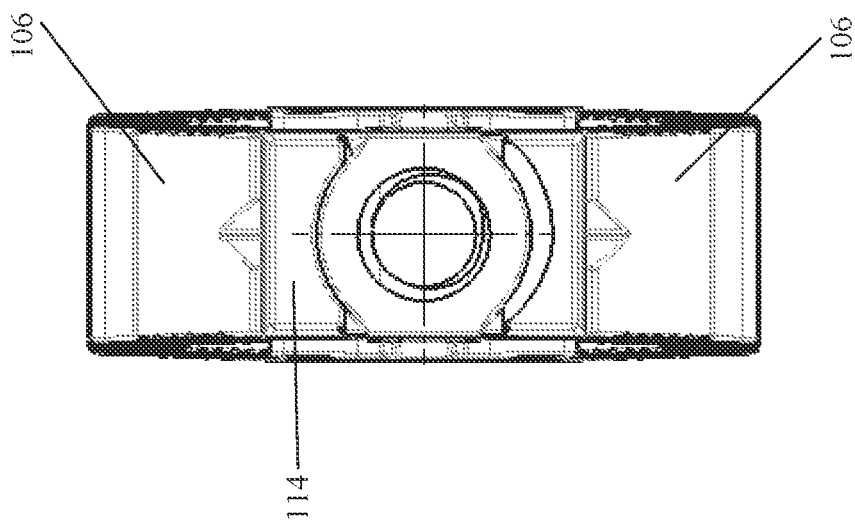
Figure 2D:
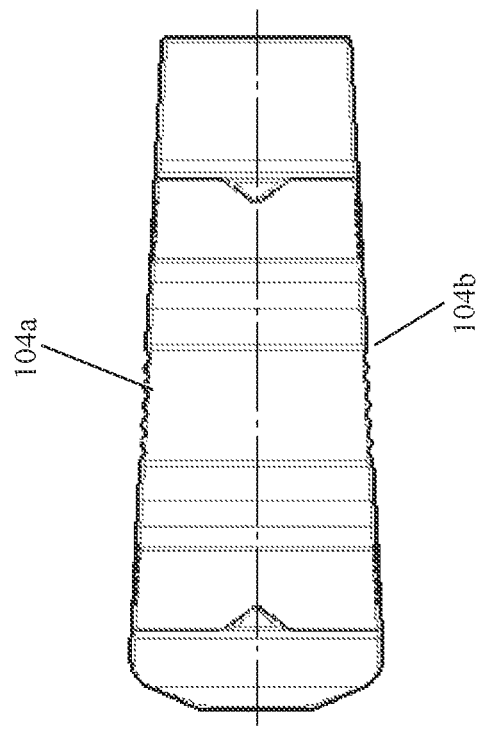
Figure 2C:
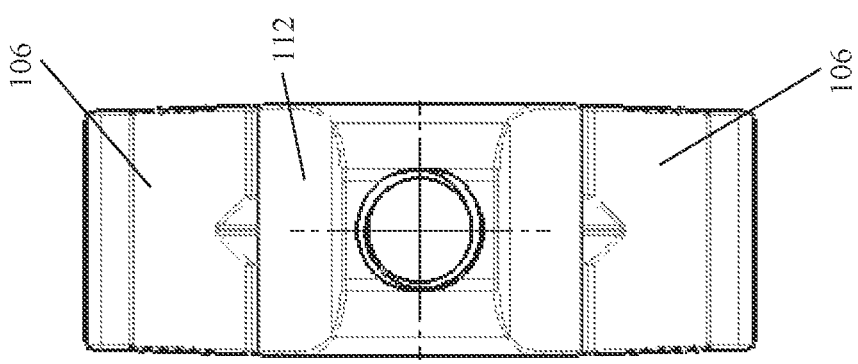

Adjacent body segments can further include interlocking projections 126 and slots 128 that mate in a tongue and groove configuration when the device is expanded (See FIG. 1F). For example, each of the first end body segment 112 and second end body segment 114 can include a pair of projections 126 on opposing sides of the segment that mate with corresponding slots 128 in the adjacent side body segment 106. Side body segments 106 can similarly include one or more projections 126 and/or slots 128 for interlocking with adjacent segments. In the depicted embodiment, each side body segment 106 includes a centrally located projection 126 on a first side of the segment and a centrally located slot 128 on an opposing side of the segment. Once the device body 102 is expanded, the interlocking tongue and groove connection of projections 126 and slots 128 strengthens the implant against shear and torsional forces in the patient's body.

Figure 6B:
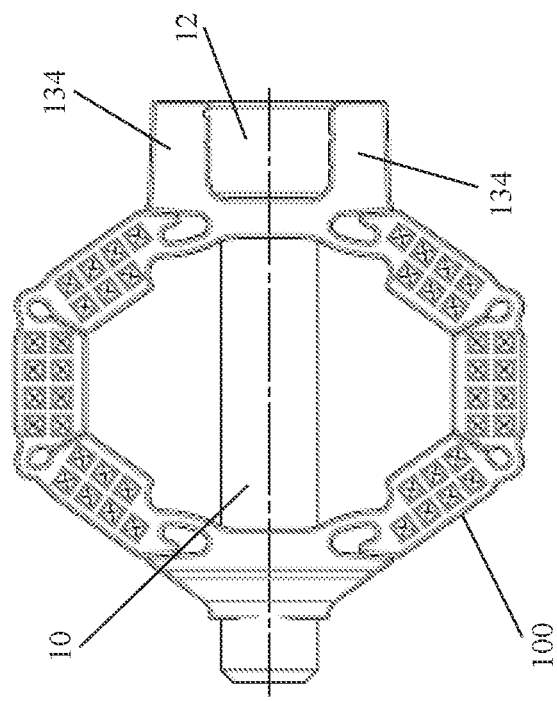
FIGS. 6A-6B depict an expandable intervertebral body fusion device according to an embodiment.
Figure 6A:
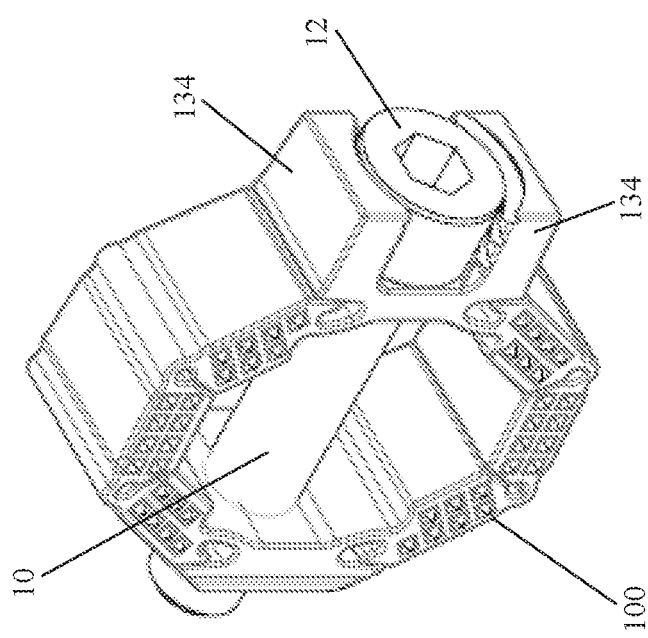

Each of first end body segment 112 and second end body segment 114 can include an opening that aids in insertion and/or expansion of device. In one embodiment, second end body segment 114 includes a second opening 130 and first end body segment 112 includes a first opening 132. A stabilizing element, such as a screw 10 (See FIGS. 6A-6B) can extend through second opening 130 and locking bushing 118 and into the first opening 132, which, in the case of the stabilizing element being a screw, may be threaded to interface with the threads of the screw. Second end body segment 114 can further include a pair of flanges 134 that define an opening 136 in which a screw head 12 of a stabilizing screw 10 can be contained. Flanges 134 can also define outer gripping surfaces that can be engaged by an insertion element used to insert the device 100 into the patient's body. In some embodiments, first end body segment 112 can be tapered to facilitate insertion of the device 100 into the disc space through the minimally invasive access opening.

FIGS. 2A-2E depict device 100 in an expanded configuration. As the device 100 is expanded, the mediolateral body segments 106 on opposing sides of the device body 102 are moved away from each other causing the device to expand medially and laterally within the disc space and therefore providing a larger area to facilitate bone growth within the device. The device 100 can be expanded until the locking bushing 118 reaches the proximal side of the first end body segment 112 such that the locking projections 120 of the locking bushing 118 nest into the lock apertures 122 in the first end body segment 112. As can be seen in these figures, expanded device provides a continuous outer perimeter having a greater width (i.e., mediolateral width when the device is horizontal expanded) between side body segments 106 and a corresponding larger interior 116 into which bone growth promoting material can be inserted through first opening 130 and openings in locking bushing 118. In some embodiments, the bushing end 120 locks permanently into the lock apertures 122 via locking phalanges stabilizing the implant with the need of a stabilizing screw. In other embodiments, a stabilizing screw 10 can be inserted through device and extend through second opening and be threadedly engaged with first opening 132 to provide further support and stability for device in vivo (See FIGS. 6A-6B). In some embodiments, a head of such a screw may be contained between flanges 134. In other embodiments, the device 100 may remain in the body with no screw or other supporting member extending through device.

Figure 4A:
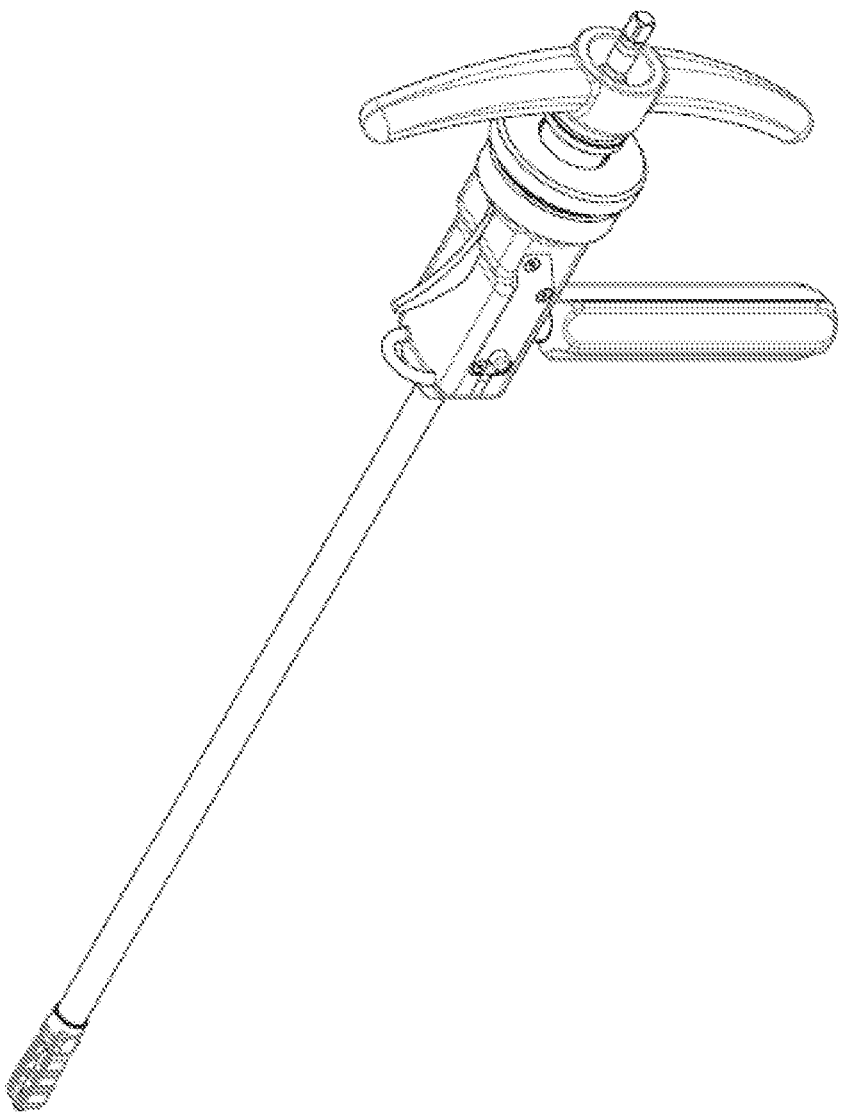
FIGS. 4A-4C depict a device for inserting and expanding and expandable intervertebral body fusion device according to an embodiment.
Figure 4B:
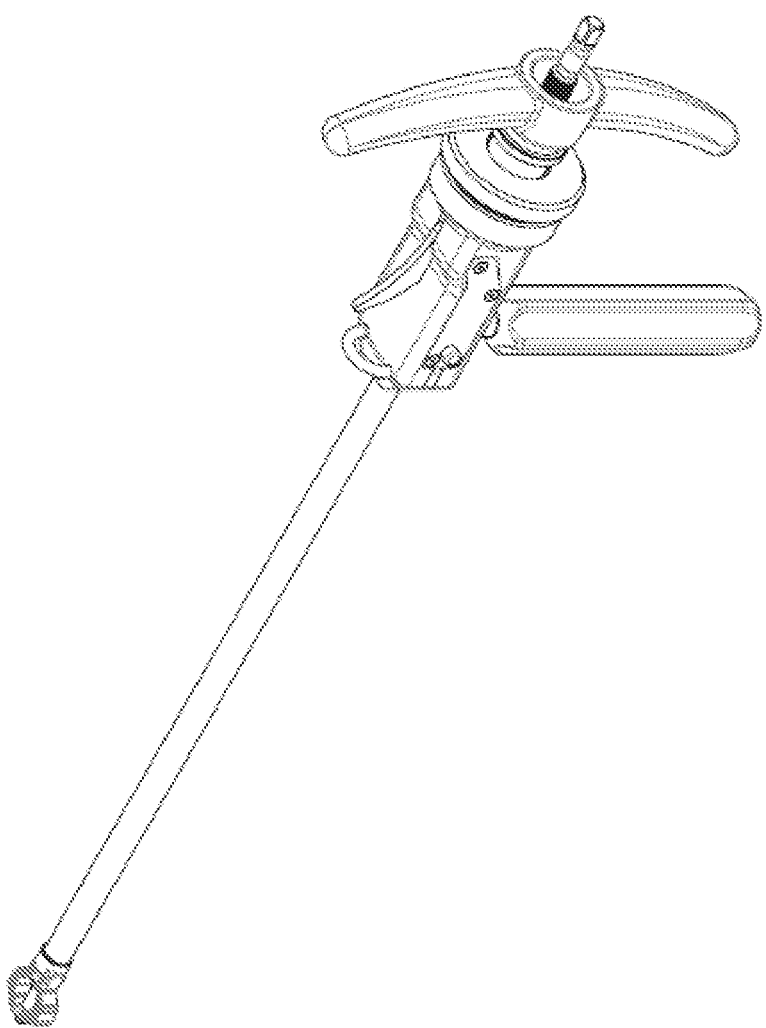
Figure 4C:
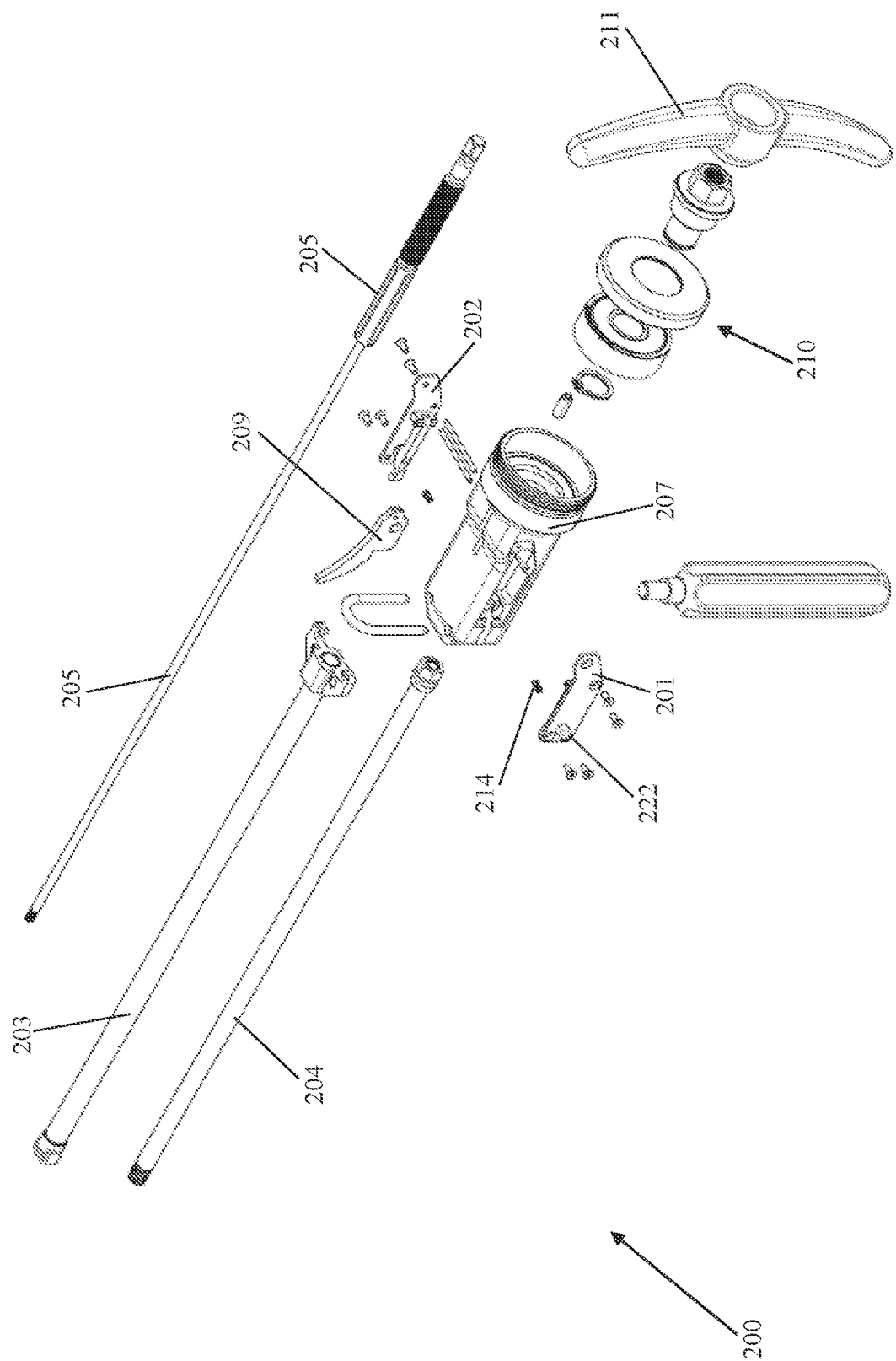

FIGS. 4A-4C depicts an embodiment of an insertion device 200 that can be used to expand an expandable intervertebral body fusion device as disclosed herein. The insertion device can also undo the expanded implant to its original insertion shape for removal. Insertion device can include an attachment rod 203 configured to grip the outer surfaces of flanges 134 of device 100, a stabilizing rod 204 having a threaded distal end configured to attach to the threaded inner surfaces of flanges 134 and to be extended through attachment rod 203 and an expansion rod 205 configured to be extended through stabilizing rod 204 and having a threaded distal end configured to interface with first opening 130 in device 100 to expand device. In operation, expansion rod 205 is actuated by rotating handle 211 that interfaces with expansion rod 205 and housing 207 via handle assembly 210. To prevent rotation of expansion rod 205, key lock 209 can be actuated to insert key lock 209 into a slot 220 in expansion rod 205. Rotation of handle 211 therefore causes the expansion element 205 to pull the distal end of the implant back towards the proximal end to expand the implant (note how the expansion rod has moved distally between the unexpanded implant shown in FIG. 4A and the expanded implant of FIG. 4B). The expanded implant can also be reversed into its insertions state (straightened) by rotating handle 211 counterclockwise. This would allow removal of an expanded implant after insertion into the disc space. Following expansion, one or more buttons 222 can be actuated to disengage sprint 214 loaded latches 201, 202 from housing 207, to enable housing 207 to be detached. Expansion rod 305 can also be detached by releasing the key lock and rotating the rod to disengage from the threaded distal opening of the implant. Next, the stabilizing rod 204 can be detached. One or more of bone graft and a stabilizing screw 10 (as described above) can be inserted through attachment rod 203 before the attachment rod 203 is detached to complete the insertion and expansion procedure.

Figure 5B:
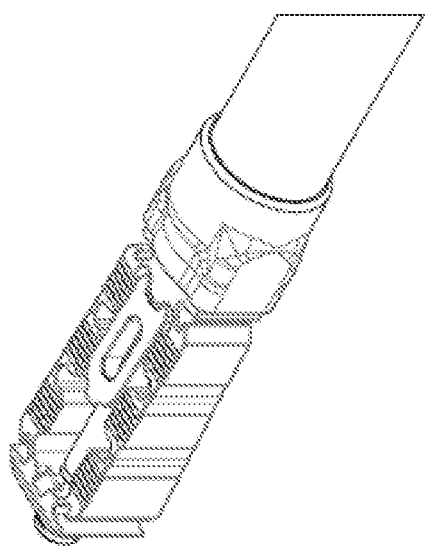
FIGS. 5A-5B depict an expandable intervertebral body fusion device interfaced with an insertion device according to an embodiment.
Figure 5A:
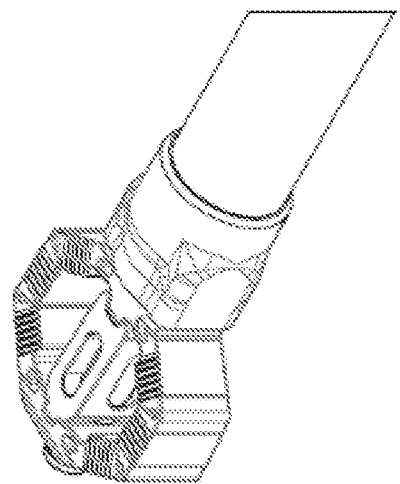

FIGS. 5A and 5B depict an implant in an unexpanded and expanded configuration, respectively, interfaced with insertion device.

As noted above, device 100 can be inserted between adjacent vertebrae on its side, with bearing surfaces 104a, 104b configured to interface with the vertebrae. Device 100 can be inserted in a collapsed configuration and then expanded within the disc space to occupy a greater footprint within the disc space. In embodiments, device can be inserted through the back muscles similar to the approach used for a posterior lumbar interbody fusion (PLIF) procedure. Expansion of the device then provides a large area within the device to promote bone growth similar to the size of anterior lumber interbody fusion (ALIF) procedure. Use of the device is this manner therefore enables the greater fusion capabilities of an ALIF procedure without the greater trauma and risk associated with accessing the disc space through the abdominal muscles. Other access approaches and device orientations are possible including lateral abdominal retroperitoneal insertion and anterior retroperitoneal insertion with larger sizes. Also, anterior and posterior cervical insertions with smaller sizes. One example of a type of insertion device that may be adapted for use with the cage device 100 disclosed herein is disclosed in U.S. Patent Publication No. 2.020/0281743, previously incorporated by reference herein.

In embodiments, device 100 can be 3D printed. Device can be formed from various biocompatible materials, such as, for example titanium.

In a further embodiment, the central bushing can expand vertically after expansion of the implant providing height expansion. In embodiments, the bushing can have a central core with phalanges connected by flexures. When the device is opened, it expands the central core. Another option is flexure phalanges that cover the upper and lower endplates.

Various embodiments of systems, devices, and methods have been described herein. These embodiments are given only by way of example and are not intended to limit the scope of the claimed inventions. It should be appreciated, moreover, that the various features of the embodiments that have been described may be combined in various ways to produce numerous additional embodiments. Moreover, while various materials, dimensions, shapes, configurations and locations, etc. have been described for use with disclosed embodiments, others besides those disclosed may be utilized without exceeding the scope of the claimed inventions.

Persons of ordinary skill in the relevant arts will recognize that the subject matter hereof may comprise fewer features than illustrated in any individual embodiment described above. The embodiments described herein are not meant to be an exhaustive presentation of the ways in which the various features of the subject matter hereof may be combined. Accordingly, the embodiments are not mutually exclusive combinations of features; rather, the various embodiments can comprise a combination of different individual features selected from different individual embodiments, as understood by persons of ordinary skill in the art. Moreover, elements described with respect to one embodiment can be implemented in other embodiments even when not described in such embodiments unless otherwise noted.

Although a dependent claim may refer in the claims to a specific combination with one or more other claims, other embodiments can also include a combination of the dependent claim with the subject matter of each other dependent claim or a combination of one or more features with other dependent or independent claims. Such combinations are proposed herein unless it is stated that a specific combination is not intended.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims, it is expressly intended that the provisions of 35 U.S.C. § 112(f) are not to be invoked unless the specific terms "means for" or "step for" are recited in a claim.

The invention claimed is:

1. An expandable intervertebral body fusion device, comprising:
   a unitary monolithic body, the body having a plurality of body segments connected to each other with flexure members and an opening defined between the plurality of body segments, including—
   an anterior body segment;
   a posterior body segment;
   one or more mediolateral body segments extending between the anterior body segment and the posterior body segment along both a lateral side and a medial side of the anterior body segment and the posterior body segment;
   an opening formed in each of the anterior body segment and the posterior body segment; and
   a locking bushing extending from one of the anterior body segment and the posterior body segment into the opening in the body,
   wherein the body is configured to be mediolaterally expanded from a compressed configuration to an expanded configuration by interaction of an expansion tool with at least one of the openings in the anterior body segment and posterior body segment causing the one or more mediolateral body segments on the lateral side and the one or more mediolateral body segments on the medial side to generally move away from each other and expand the opening between the plurality of body segments such that the body forms a greater mediolateral footprint in the expanded configuration than in the compressed configuration, and wherein further expansion of the body is prevented by interaction of the locking bushing with the other of the anterior body segment and the posterior body segment such that an axial length of the locking bushing predetermines and limits an amount of expansion of the body.

2. The expandable intervertebral body fusion device of claim 1, wherein the locking bushing includes an opening in communication with the opening of the one of the anterior body segment and posterior body segment from which it extends.

3. The expandable intervertebral body fusion device of claim 1, wherein the locking bushing includes a locking projection configured to interface with a corresponding slot in the other one of the anterior body segment and posterior body segment.

4. The expandable intervertebral body fusion device of claim 3, wherein the locking bushing includes a pair of locking projections on opposing sides of the locking bushing configured to interface with a pair of corresponding slots.

5. The expandable intervertebral body fusion device of claim 1, wherein the locking bushing is unitarily formed with the body.

6. The expandable intervertebral body fusion device of claim 1, wherein the locking bushing is attached to the body with the expansion tool.

7. The expandable intervertebral body fusion device of claim 6, further comprising a plurality of locking bushings having different axial lengths, wherein each different axial length is configured to permit a predetermined amount of expansion of the body.

8. The expandable intervertebral body fusion device of claim 1, wherein the mediolateral body segments include adjacent projections and grooves that form tongue and groove connections between adjacent mediolateral body segments when the body is in the expanded configuration, the tongue and groove connections providing increased resistance of the body to shear and torsional forces.

9. The expandable intervertebral body fusion device of claim 8, wherein the anterior body segment and posterior segment also form tongue and groove connections with adjacent mediolateral body segments.

10. The expandable intervertebral body fusion device of claim 1, wherein the locking bushing is configured to be expanded vertically following mediolateral expansion of the body.

11. An expandable intervertebral body fusion device, comprising:
a unitary monolithic body, the body having a plurality of body segments connected to each other with flexure members and an opening defined between the plurality of body segments, including—
an anterior body segment;
a posterior body segment;
one or more mediolateral body segments extending between the anterior body segment and the posterior body segment along both a lateral side and a medial side of the anterior body segment and the posterior body segment; and
an opening formed in each of the anterior body segment and the posterior body segment; and
wherein the body is configured to be mediolaterally expanded from a compressed configuration to an expanded configuration by interaction of an expansion tool with at least one of the openings in the anterior body segment and posterior body segment causing the one or more mediolateral body segments on the lateral side and the one or more mediolateral body segments on the medial side to generally move away from each other and expand the opening between the plurality of body segments such that the body forms a greater mediolateral footprint in the expanded configuration than in the compressed configuration,
further comprising a locking bushing extending from one of the anterior body segment and the posterior body segment into the opening in the body, and wherein further expansion of the body is prevented by interaction of the locking bushing with the other of the anterior body segment and the posterior body segment, and further comprising a plurality of locking bushings having different axial lengths, wherein each different axial length is configured to permit a predetermined amount of expansion of the body.

12. The expandable intervertebral body fusion device of claim 11, wherein the locking bushing includes an opening in communication with the opening of the one of the anterior body segment and posterior body segment from which it extends.

13. The expandable intervertebral body fusion device of claim 11, wherein the locking bushing includes a locking projection configured to interface with a corresponding slot in the other one of the anterior body segment and posterior body segment.

14. The expandable intervertebral body fusion device of claim 13, wherein the locking bushing includes a pair of locking projections on opposing sides of the locking bushing configured to interface with a pair of corresponding slots.

15. The expandable intervertebral body fusion device of claim 11, wherein the locking bushing is unitarily formed with the body.

16. The expandable intervertebral body fusion device of claim 11, wherein the locking bushing is attached to the body with the expansion tool.

17. An expandable intervertebral body fusion device, comprising:
a unitary monolithic body, the body having a plurality of body segments connected to each other with flexure members and an opening defined between the plurality of body segments, including—
an anterior body segment;
a posterior body segment;
one or more mediolateral body segments extending between the anterior body segment and the posterior body segment along both a lateral side and a medial side of the anterior body segment and the posterior body segment; and
an opening formed in each of the anterior body segment and the posterior body segment; and
wherein the body is configured to be mediolaterally expanded from a compressed configuration to an expanded configuration by interaction of an expansion tool with at least one of the openings in the anterior body segment and posterior body segment causing the one or more mediolateral body segments on the lateral side and the one or more mediolateral body segments on the medial side to generally move away from each other and expand the opening between the plurality of body segments such that the body forms a greater mediolateral footprint in the expanded configuration than in the compressed configuration,
further comprising a locking bushing extending from one of the anterior body segment and the posterior body segment into the opening in the body, and wherein further expansion of the body is prevented by interaction of the locking bushing with the other of the anterior body segment and the posterior body segment, and, wherein the locking bushing is configured to be expanded vertically following mediolateral expansion of the body.

* * * * *